(12) United States Patent
Xin et al.

(10) Patent No.: US 9,970,870 B2
(45) Date of Patent: May 15, 2018

(54) RECONFIGURABLE REFLECT-ARRAY TO REALIZE TASK-SPECIFIC COMPRESSIVE SENSING IN SCREENING APPLICATIONS

(71) Applicant: ARIZONA BOARD OF REGENTS ON BEHALF OF THE UNIVERSITY OF ARIZONA, Tucson, AZ (US)

(72) Inventors: Hao Xin, Tucson, AZ (US); Min Liang, Tucson, AZ (US); Mark A. Neifeld, Tucson, AZ (US); Tim Harvey, Fairfax, VA (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days. days.

(21) Appl. No.: 15/451,160

(22) Filed: Mar. 6, 2017

(65) Prior Publication Data

US 2017/0254750 A1     Sep. 7, 2017

Related U.S. Application Data

(60) Provisional application No. 62/303,772, filed on Mar. 4, 2016.

(51) Int. Cl.
| | |
|---|---|
| *G01B 11/24* | (2006.01) |
| *G01N 21/55* | (2014.01) |
| *H03M 7/30* | (2006.01) |
| *G01V 8/00* | (2006.01) |
| *G01N 22/00* | (2006.01) |

(52) U.S. Cl.
CPC ............ *G01N 21/55* (2013.01); *G01N 22/00* (2013.01); *G01V 8/005* (2013.01); *H03M 7/30* (2013.01); *H03M 7/3062* (2013.01); *G01N 2201/123* (2013.01); *G01N 2201/126* (2013.01)

(58) Field of Classification Search
CPC ............ G01N 21/55; G01N 2201/123; G01N 2201/126; H03M 7/30
USPC .................................................. 356/600–624
See application file for complete search history.

(56) References Cited

U.S. PATENT DOCUMENTS

| | | |
|---|---|---|
| 6,195,047 B1 | 2/2001 | Richards |
| 6,384,787 B1 | 5/2002 | Kim et al. |
| 6,765,535 B1 | 7/2004 | Brown et al. |

OTHER PUBLICATIONS

J. Hunt et al, "Metamaterial Apertures for Computational Imaging" Science, vol. 339, pp. 310-313, 2013.

(Continued)

*Primary Examiner* — Tri T Ton
(74) *Attorney, Agent, or Firm* — Nguyen & Tarbet Patent Law Firm

(57) ABSTRACT

A threat detection system having a reconfigurable reflect-array and compressive sensing unit to effectively detect objects that are a threat is presented. A statistical library, having a wide range of threat and non-threat examples and capable of incorporating new examples while being used, is utilized by several optimization algorithms to calculate an optimal illumination pattern for compressive sensing detection. The reflect-array is configured to produce the optimal illumination pattern via a plurality of reflect-array elements. In this way, a plurality of data may be parallel processed, thereby increasing the detection speed and reducing cost.

20 Claims, 18 Drawing Sheets
(1 of 18 Drawing Sheet(s) Filed in Color)

(56) References Cited

OTHER PUBLICATIONS

J.M. Bioucas-Dias, and M.A. Figueiredo, "A New Twist: Two-Step Iterative Shrinkage/Thresholding Algorithms for Image Restoration," IEEE Trans. Image Process. 16, pp. 2992-3004, 2007.

O. M. Bucci, G. Mazzarella and G. Panariello, "Reconfigurable Arrays by Phase-Only Control," IEEE Trans. on Antennas and Propagation, vol. 39, No. 7, pp. 919-925, 1991.

M.A. Neifeld and P. Shankar, "Feature-specific imaging," Appl. Opt., vol. 42, 3379-3389 (2003).

Payam Nayeri, Min Liang, Rafael Austreberto Sabory-Garc'ia, Mingguang Tuo, Fan Yang, Michael Gehm, Hao Xin and Atef Z. Elsherbeni "3D Printed Dielectric Reflectarrays: Low-Cost High-Gain Antennas at Sub-Millimeter Waves" IEEE Trans. on Antennas and Propagation, vol. 62, No. 4, Apr. 2014.

Xin, Hao, et. al, "Reconfigurable Array Design to Realize Principal Component Analysis (PCA) Based Microwave Compressive Sensing Imaging System", IEEE Antennas and Wireless Propagation Letters, Jan. 2015.

M.R. Chaharmir, J. Shaker, M. Cuhaci, and A. Ittipiboon. "Broadband Reflectarray Antenna with Double Cross Loops." Electronics Letters, vol. 42, Issue 2, Jan. 19, 2006, pp. 65-66.

P. H. Siegel, "Terahertz technology," IEEE Trans. Microwave Theory Tech., vol. 50, No. 3, pp. 910-928, Mar. 2002.

P. H. Siegel, P. De Maagt, and A. I. Zaghloul, "Antennas for terahertz applications," presented at the IEEE Antennas and Propagation Society Int. Symp., Albuquerque, NM, USA, Jul. 2006.

D.M. Pozar, S. D. Targonski, and H. D. Syrigos, "Design of millimeterwave microstrip reflectarrays," IEEE Trans. Antennas Propag., vol. 45, No. 2, pp. 287-296, Feb. 1997.

J. A. Encinar and J. A. Zornoza, "Three-layer printed reflectarrays for contoured beam space applications," IEEE Trans. Antennas Propag., vol. 52, No. 5, pp. 1138-1148, May 2004.

P. Nayeri, F. Yang, and A. Z. Elsherbeni, "A broadband reflectarray using sub-wavelength patch elements," presented at the IEEE Antennas and Propagation Society Int. Symp., Charleston, SC, USA, Jun. 2009.

M. E. Bialkowski and K. H. Sayidmarie, "Investigations into phase characteristics of a single-layer reflectarray employing patch or ring elements of variable size," IEEE Trans. Antennas Propag., vol. 56, No. 11, pp. 3366-3372, Nov. 2008.

A. Tamminen, S. Makela, J. Ala-Laurinaho, J. Hakli, P. Koivisto, P. Rantakari, J. Saily, A. Luukanen, and A. V. Raisanen, "Reflectarray design for 120-GHz radar application: Measurement results," IEEE Trans. Antennas Propag., vol. 61, No. 10, pp. 5036-5047, Oct. 2013.

J. C. Ginn, B. A. Lail, and G. D. Boreman, "Phase characterization of reflectarray elements at infrared," IEEE Trans. Antennas Propag., vol. 55, No. 11, pp. 2989-2993, Nov. 2007.

F. Yang, P. Nayeri, A. Z. Elsherbeni, J. C. Ginn, D. Shelton, G. Boreman, and Y. Rahmat-Samii, "Reflectarray design at infrared frequency: Effects and models of material loss," IEEE Trans. Antennas Propag., vol. 60, No. 9, pp. 4202-4209, Sep. 2012.

T. Niu, W. Withayachumnankul, B. S.-Y. Ung, H. Menekse, M. Bhaskaran, S. Sriram, and C. Fumeaux, "Experimental demonstration of reflectarray antennas at terahertz frequencies," Opt. Expr., vol. 21, No. 3, pp. 2875-2889, Feb. 2011.

P. Nayeri, M. Liang, R. Sabory-Garc'ia, M. Tuo, F. Yang, M. Gehm, H. Xin, and A. Elsherbeni, "High gain dielectric reflectarray antennas for THz applications," presented at the IEEE Antennas and Propagation Society Int. Symp., Orlando, FL, USA, Jul. 2013.

S. H. Zainud-Deen, S. M. Gaber, A. M. Abd-Elhady, K. H. Awadalla, and A. A. Kishk, "Perforated dielectric resonator antenna reflectarray," ACES J., vol. 26, No. 10, 2011.

L. Zou, W. Withayachumnankul, C. M. Shah, A. Mitchell, M. Bhaskaran, S. Sriram, and C. Fumeaux, "Dielectric resonator nanoantennas at visible frequencies," Opt. Expr., vol. 21, No. 1, pp. 1344-1352, Jan. 2013.

H. Rajagopalan and Y. Rahmat-Samii, "Dielectric and conductor loss quantification for microstrip reflectarray: Simulations and measurements," IEEE Trans. Antennas Propag., vol. 56, No. 4, pp. 1192-1196, Apr. 2008.

H. Rajagopalan and Y. Rahmat-Samii, "On the reflection characteristics of a reflectarray element with low-loss and high-loss substrates," IEEE Antennas Propag. Mag., vol. 52, No. 4, pp. 73-89, Aug. 2010.

K. C. Kao and G. A. Hockham, "Dielectric-fibre surface waveguides for optical frequencies," Proc. IEE, vol. 113, No. 7, pp. 1151-1158, Jul. 1966.

Z. Wu, J. Kinast, M. Gehm, and H. Xin, "Rapid and inexpensive fabrication of terahertz electromagnetic bandgap structures," Opt. Expr., vol. 16, No. 21, pp. 16442-16451, Oct. 2008.

Z. Wu, A. Young, M. Gehm, and H. Xin, "Investigation of several terahertz electromagnetic bandgap structures," Microw. Opt. Tech. Lett., vol. 52, No. 3, pp. 678-686, Dec. 2010.

[Online]. Available: http://www.2objet.com/Default.aspxObjetTM.

D. R. Reid and G. S. Smith, "A full electromagnetic analysis of grooved-dielectric Fresnel zone plate antennas for microwave and millimeter-wave," IEEE Trans. Antennas Propag., vol. 55, No. 8, pp. 2138-2146, Aug. 2007.

P. Nayeri, F. Yang, and A. Z. Elsherbeni, "Broadband reflectarray antennas using double-layer subwavelength patch elements," IEEE Antennas Propag. Lett., vol. 9, pp. 1139-1142, 2010.

Ansys HFSS v15.0, Ansys Inc., 2013.

CST Microwave Studio, CST Studio Suite 2012 Computer SimulationTechnology AG.

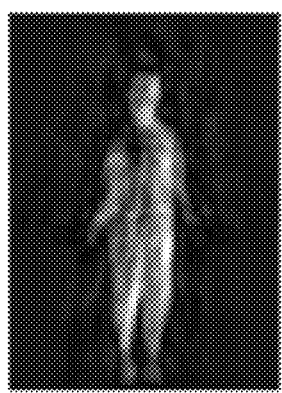
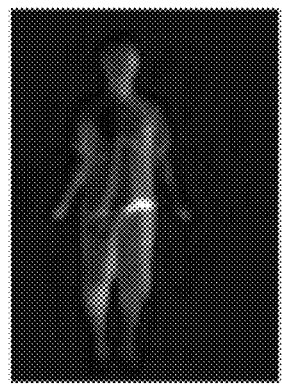
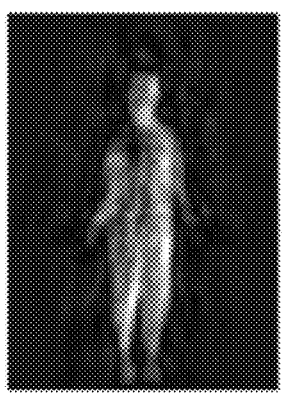
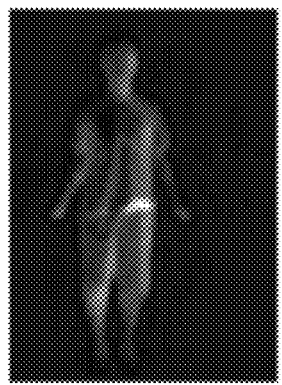
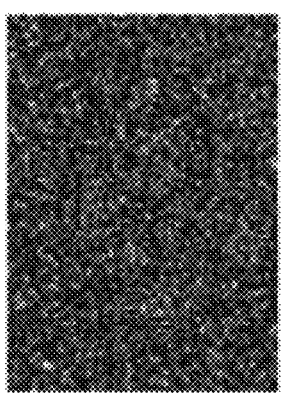
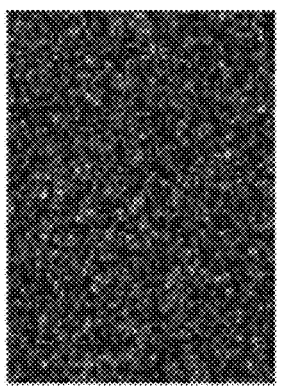
FIG. 5A     FIG. 5B     FIG. 5C

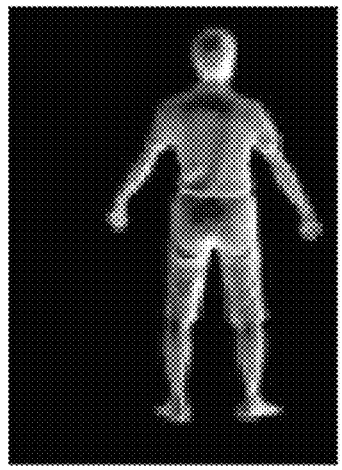  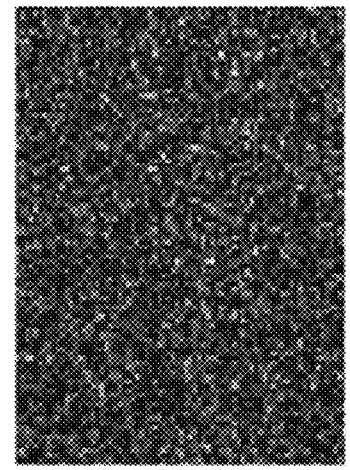
FIG. 12A  FIG. 12B  FIG. 12C
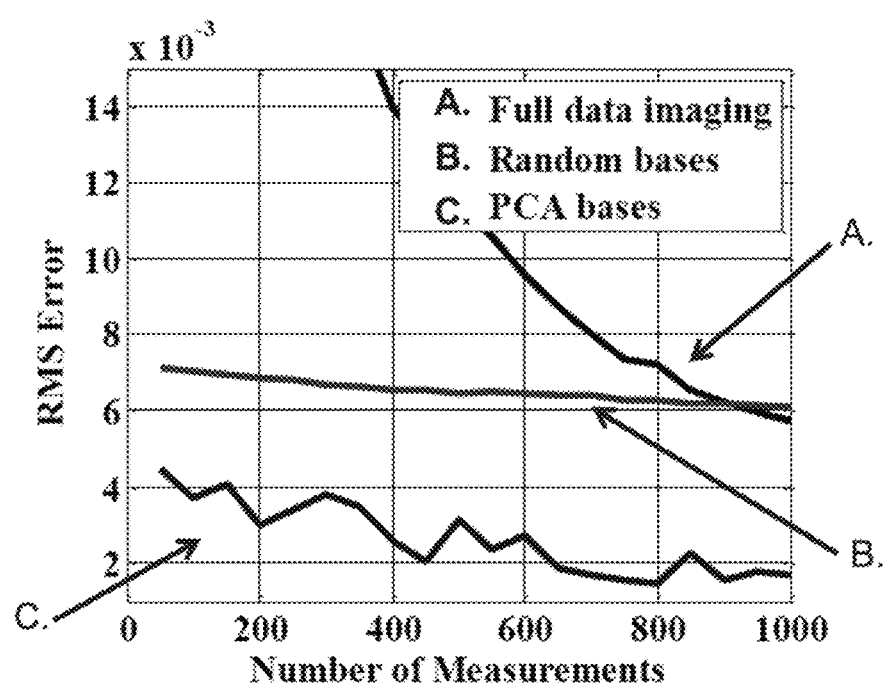
FIG. 13

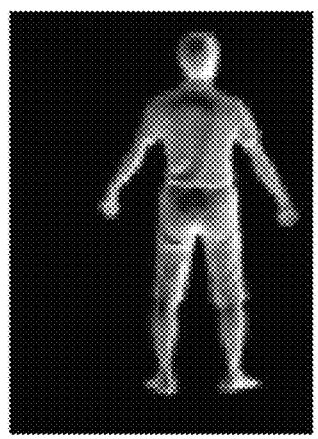 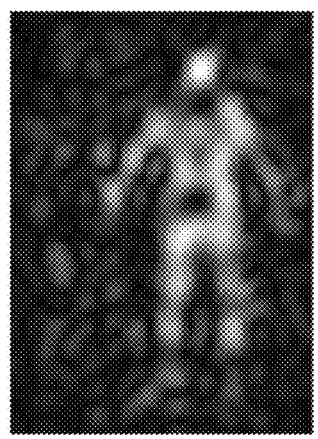 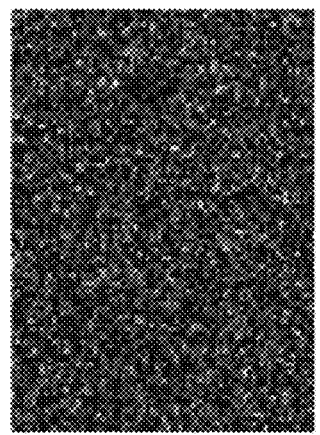
FIG. 14A          FIG. 14B          FIG. 14C
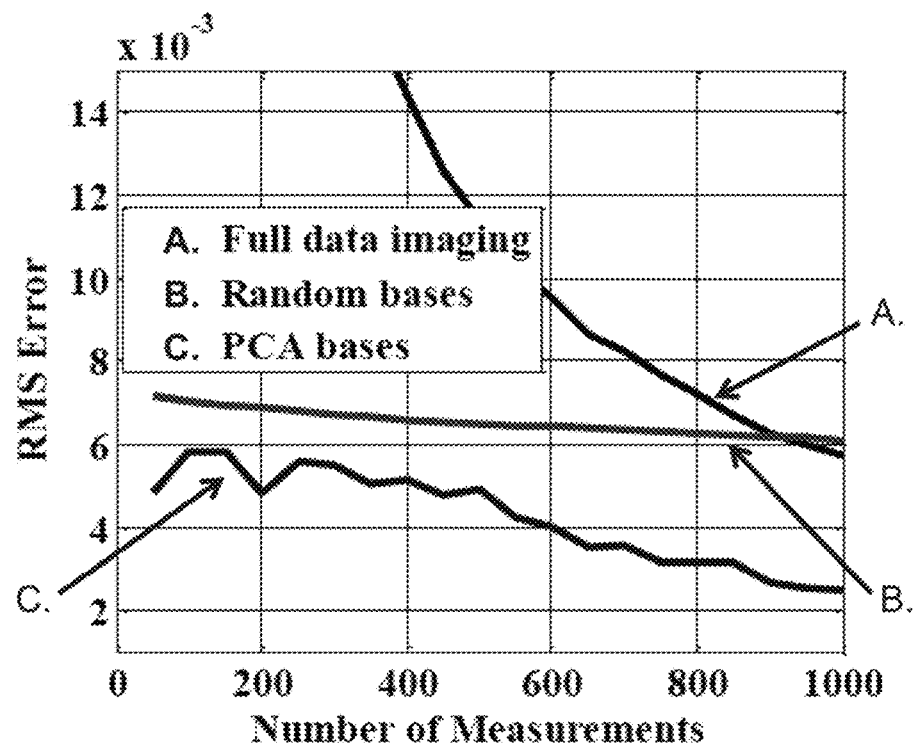
FIG. 15

RECONFIGURABLE REFLECT-ARRAY TO REALIZE TASK-SPECIFIC COMPRESSIVE SENSING IN SCREENING APPLICATIONS

CROSS REFERENCE

This application claims priority to U.S. Patent Application No. 62/303,772, filed Mar. 4, 2016, the specification(s) of which is/are incorporated herein in their entirety by reference.

FIELD OF THE INVENTION

The present invention relates to employing compressive sensing in reconfigurable reflect-array detection systems for standoff security scanning of threat objects, where threat objects include, but are not limited to, weapons, explosives, liquids, gels, etc.

BACKGROUND OF THE INVENTION

Compressive sensing is a novel sampling/sensing paradigm that enables significant reduction in sampling and computation costs for signals with sparse or compressible representation. This technique has experienced rapid growth in recent years and has attracted attention in electrical engineering, optics, signal processing, statistics and computer science. Using compressive sensing techniques, the number of measurements needed to construct an image of a scanned object is greatly reduced compared to traditional methods, particularly when the signal is sparse in a known basis. The fundamental idea behind compressive sensing is, rather than first sampling at a high rate followed by compressing the sampled data, an improvement in data recovery is obtained when the data is directly sampled. Compression is achieved with direct sampling, resulting in an output data in a compressed format. For example, efficient sampling protocols may be designed to capture small amounts of useful signal information in a sparse domain. After sampling, the full-length signal is reconstructed using numerical optimization algorithms.

Compressive sensing techniques have been applied to microwave imaging systems employing a guided wave metamaterial aperture to generate different radiation patterns for compressive sensing. The reconstruction of compressive images at 10 frames per second was achieved at K-band. However, the radiation patterns generated by the metamaterial aperture were random and the sampling protocol was not optimized to capture the signal information. In the present invention, a plurality of optimization algorithms are used to create a plurality of optimized projections. An optimized radiation pattern based on the plurality of optimized projections, as opposed to a random radiation pattern, can then be realized. One such optimization algorithm is the Principal Component Analysis ("PCA") as detailed in "Reconfigurable Array Design to Realize Principal Component Analysis (PCA) Based Microwave Compressive Sensing Imaging System", Xin et al, which is incorporated herein in its entirety.

PCA is one of the most commonly used tools in statistics and data-mining areas for compression and classification of data. The purpose of PCA is to reduce the dimensionality of a data set having a large number of interrelated variables by transforming it to a new set having a smaller number of variables, while retaining as much of the sample information as possible [3]. These new variables, called principal components ("PCs"), are uncorrelated and ordered by the fraction of the total information each retains. Therefore, keeping only the values of the first few principal components would still retain most of the information from all the original variables. In practice, this PCA is achieved by calculating the covariance matrix of the full data set. The eigenvectors and eigenvalues of the covariance matrix are then computed and sorted according to decreasing eigenvalues. Compared to a random-pattern-based compressive sensing system, fewer numbers of measurements are required for optimized-radiation-pattern-based compressive sensing systems (such as the PCA based system) to achieve the same performance.

A direct application of the present invention would be security screening systems at places such as airports, train stations, or museums. The current security screening processes often encompass long lines, complex rules, and invasive methods. Further, the current security screening systems are inefficient, bulky, and costly. A faster, more accurate and cost-efficient security screening system is necessary and can be realized by the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

Traditionally, a plurality of measurements is taken, via a scanning signal, of an object during a scan. Currently existing systems and methodologies employ algorithms to detect an object and determine if said object is a threat based on these measurements. In these systems, a greater number of measurements obtained results in a more accurate determination. The currently existing systems and methodologies have inherent limitations and cannot accurately construct an image of a scanned object when the scanning signal is sparse, (e.g., when few measurements are obtained).

The present invention requires a significantly smaller number of measurements to detect an object and determine if the object is a threat based on these measurements without compromising the accuracy of the scanned image (see FIG. 6). The following non-limiting inventive features of the present invention make the construction of the scanned image possible using a reduced number of measurements:
  (1) Employing an optimized radiation pattern based on a plurality of optimized projections to scan an object—typical systems need to scan all the pixels to perform detection.
  (2) Employing a more effective algorithm, namely a compressive sensing algorithm, for processing the plurality of measurements acquired during a scan to determine whether the object poses a threat.

Application of an exemplary embodiment of the present system includes, but is not limited to, airport screening; where passengers traverse a plurality of lanes. While moving along a lane, the reflect-array panel may scan the bottom of passengers' feet to determine the presence of a threat object.

BRIEF DESCRIPTION OF THE DRAWINGS

This patent application contains at least one drawing executed in color. Copies of this patent or patent application publication with color drawing(s) will be provided by the Office upon request and payment of the necessary fee.

FIGS. 5A-5C show compressive sensing reconstructed images using 200 measurement values for original object images without (top) and with (bottom) threat. FIG. 5A shows the original image. FIG. 5B shows the reconstructed image using ideal PCA generated bases. FIG. 5C shows the reconstructed image using randomly generated bases.

FIGS. 12A-12C show the compressive sensing reconstructed image using 200 reconfigurable array synthesized patterns. FIG. 12A shows the original image. FIG. 12B shows the reconstructed image using 200 reconfigurable array generated patterns with both amplitude and phase controls. FIG. 12C shows the reconstructed image using 200 random bases.

FIG. 13 shows the RMS error of the reconstructed image using full data imaging method and the compressive sensing method with random bases and reconfigurable array generated PCA bases using both amplitude and phase controls.

FIGS. 14A-14C show the compressive sensing reconstructed image using 200 reconfigurable array synthesized patterns. FIG. 14A shows the original image. FIG. 14B shows the reconstructed image using 200 reconfigurable array generated patterns with phase only control. FIG. 14C shows the reconstructed image using 200 random bases.

FIG. 15 shows the RMS error of the reconstructed image using full data imaging method and the compressive sensing method with random bases and reconfigurable array generated PCA bases using phase only control.

DETAILED DESCRIPTION OF INVENTION

Figure 1:
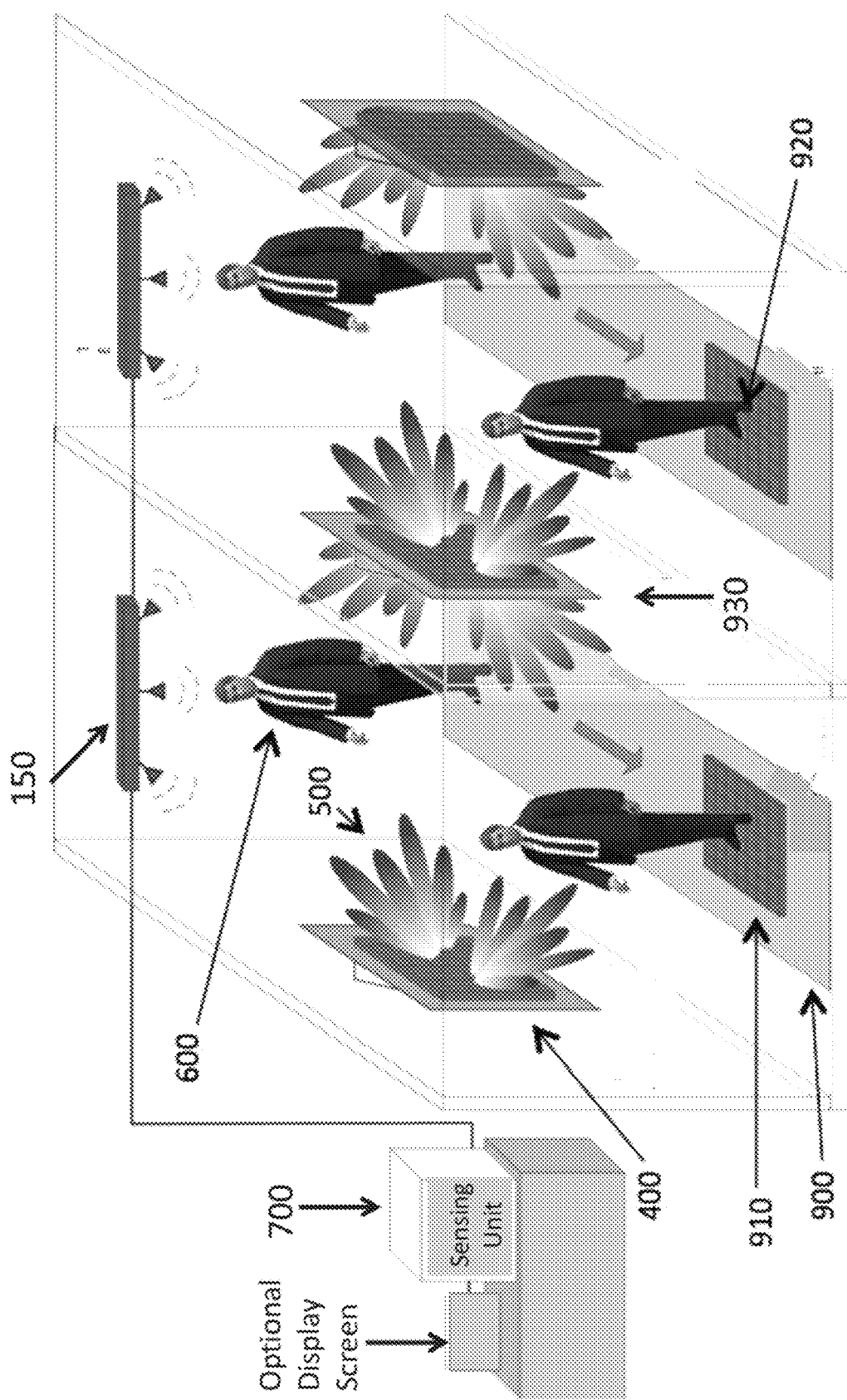
FIG. 1 shows a diagrammatic representation of the threat detection system of the present invention.
Figure 2:
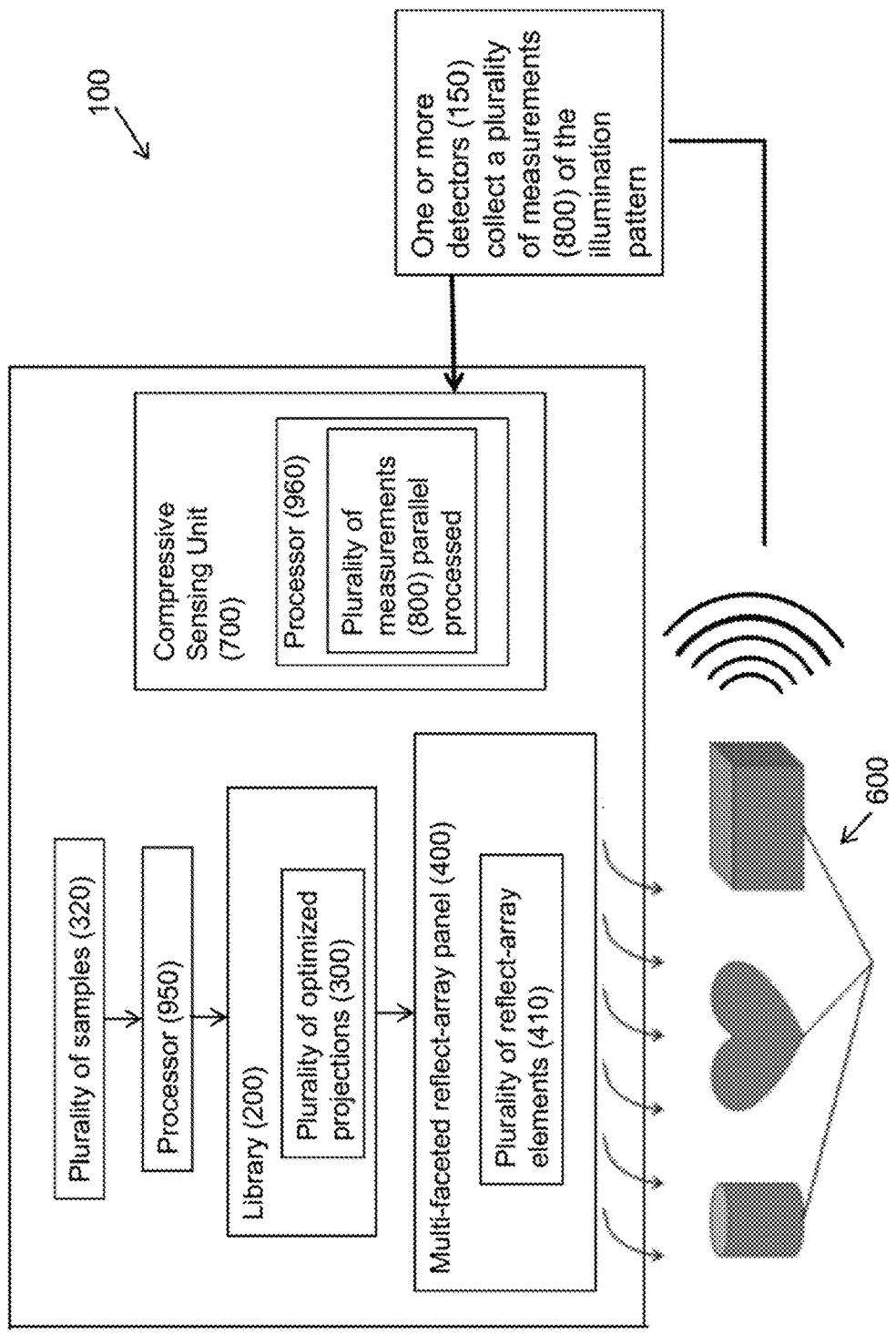
FIG. 2 is a flowchart detailing an embodiment of the threat detection system.

Referring now to FIGS. 1-21, the present invention features a reflect-array based threat detection system (100) providing a faster, more accurate and cost-efficient solution to current security screening processes by employing compressive sensing to effectively determine whether or not an object is a threat. In some embodiments, the threat detection system (100) comprises a first processor (950) configured to generate a plurality of optimized projections (300) by executing a first optimization algorithm using a plurality of samples (320). These samples (320) may be acquired from an external database. In alternate embodiments, the plurality of samples (320) may be stored in a system database, herein referred to as the library (200), operatively coupled to the first processor (950). In further embodiments, the plurality of samples (320) may comprise objects that pose a threat and objects that do not pose a threat. In supplementary embodiments, the library (200) also stores the plurality of optimized projections (300).

In some embodiments, the first optimization algorithm may be realized using Principle Component Analysis, Fisher Linear Discriminant Method, Support Vectors Method, Information Optimal Method, or the K-nearest Neighbor Method individually or in combination. The first optimization algorithm may process the plurality of samples (320) using one (or a combination) of the aforementioned techniques in order to extract key components that characterize threat objects. These key components are embodied by the plurality of optimized projections (300), which are subsequently used to distinguish threat objects from non-threat objects.

The threat detection system (100) may further feature a reflect-array panel (400) emitting a synthesized radiation (500) in a plurality of directions to scan an object (600) of interest. In other embodiments, other array types (e.g. a metamaterial antenna array or phased array) may be employed in place of the reflect array. In some embodiments, the reflect-array panel (400) comprises a first set of reflect-array elements (410), each emitting the plurality of optimized projections (300) as a radiation pattern in one of the plurality of directions. A collective radiation results having a (multi-) directionality dependent upon the direction each reflect-array element emits its radiation pattern. This multi-directional collective radiation is the synthesized radiation (500) emitted. As a consequence of the multi-directionality, the reflect-array panel (400) is able to acquire a plurality of information about the object (600) simultaneously and parallel process this information.

In additional embodiments, reflect-array elements (410) may be devices of any geometric shape having a dielectric and a conductor (e.g. microstrips or dipoles). Additionally, each reflect-array element has a phase that may be controlled by one or more reconfigurable devices. Non-limiting examples of the reconfigurable devices are: diodes, microelectromechanical system ("MEMS") devices, or any phase changing device. The synthesized radiation (500) may be controlled by the (reconfigurable) phase of each reflect-array element.

In further embodiments, as the synthesized radiation (500) interacts with the object (600), the electromagnetic (EM) waves comprising the synthesized radiation (500) are reflected off of the object (600). These reflected EM waves are referred to as the illumination pattern of the object (600). Further, one or more detectors (150) may collect a plurality of measurements (800) of the illumination pattern and transmit the measurements (800) to a compressive sensing unit (700). The compressive sensing unit (700) processes the plurality of measurements (800) via a second processor (960) executing a compressive sensing optimization algorithm (also referred to herein as the second optimization algorithm). The second optimization algorithm may employ the optimized projections (300) as bases of measurement to determine whether or not the object (600) poses a threat. Similar to the first optimization algorithm, the second optimization algorithm may be realized using Principle Component Analysis, Fisher Linear Discriminant Method, Support Vectors Method, Information Optimal Method, or the K-nearest Neighbor Method individually or in combination.

In further embodiments, the system (100) may comprise a lane (900) having a second reflect-array panel (910) emitting a lane synthesized radiation in a set of directions to scan a second object (920). The second reflect-array panel (910) comprises a second set of reflect-array elements each emitting the plurality of optimized projections (300) as a radiation pattern in one direction, of the set of directions. Thus the lane synthesized radiation is a collective radiation comprising each radiation pattern emitted by each reflect-array element in the second set of reflect-array elements. In some embodiments, the second set of reflect-array elements may comprise devices of any geometric shape having a dielectric and a conductor.

A second illumination pattern is produced when the lane synthesized radiation is reflected off of a second object (920). In some embodiments, the second object (920) may be the bottom of human feet. A plurality of measurements of the second illumination pattern may then be acquired by the one or more detectors (150) and transmitted to the compressive sensing processing unit (700). In other embodiments the second processor (960) is further configured to execute a third optimization algorithm, which is also a compressive sensing optimization algorithm. The third optimization algorithm processes the plurality of measurements of the second illumination pattern and determines whether the second object (920) poses a threat using the optimized projections (300) as bases of measurement. The third optimization algorithm may be realized using Principle Component Analysis, Fisher Linear Discriminant Method, Support Vectors Method, Information Optimal Method, or the K-nearest Neighbor Method individually or in combination.

In some embodiments, the threat detection system (100) comprises a plurality of lanes. In other embodiments, the reflect-array panel may scan a plurality of objects.

In further embodiments, a two-sided reflect-array panel (930) is featured. This panel (930) is configured to simultaneously scan objects traversing two lanes, one on each side of the reflect-array panel (930), at the same time without requiring an increase in the number of processing components.

Since reflect-array panels allow synthesized radiation (500) to be emitted in a plurality of directions and locations, a plurality of objects (600) may be scanned at one time. These scans may then be parallel processed, resulting in a reduced hardware cost and processing speed.

Example of the Reflect-Array Based Compressive Sensing System Using PCA

As previously mentioned, each of the optimization algorithms employed by the present system may be realized via the Principle Component Analysis Method, Fisher Linear Discriminant Method, Support Vectors Method, Information Optimal Method, and the K-nearest Neighbor Method individually or in combination. The following is a non-limiting example of the present system utilizing the PCA method to detect threat objects.

I. PCA of Human Images

Figure 3:
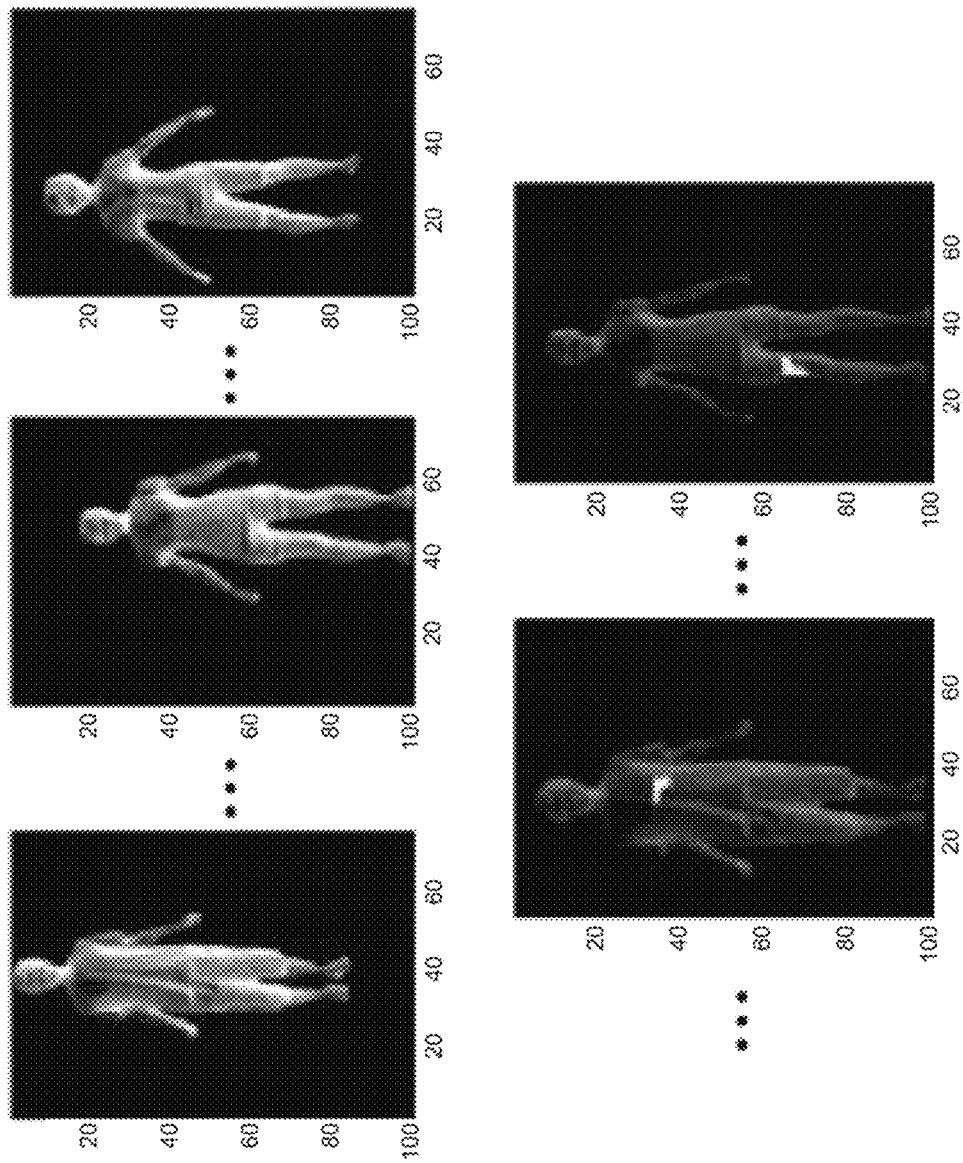
FIG. 3 shows image examples in the (statistical) library. The image size is 1.5 meters to 2 meters.
Figure 4:
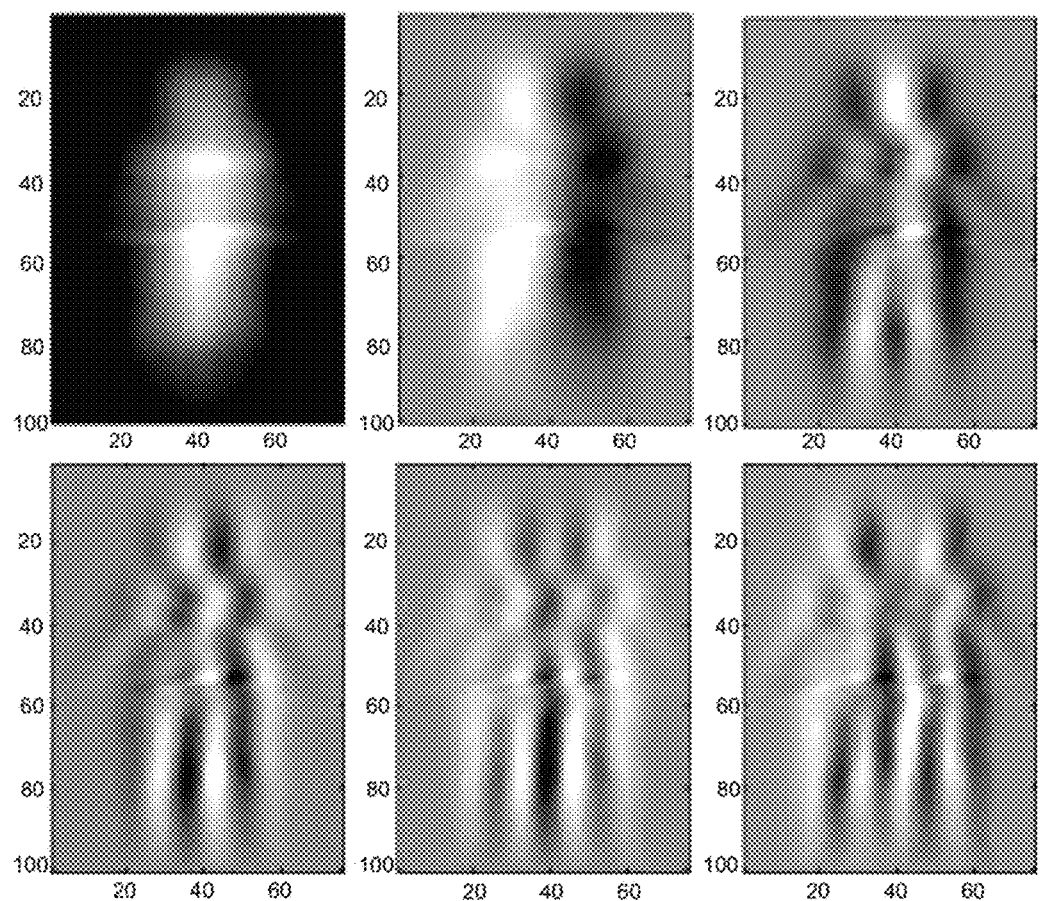
FIG. 4 shows the first six principle components from PCA using the statistical image library as shown in FIG. 3.

PCA is applied to achieve a library based compressive sensing system. Before doing compressive sensing, a statistical library that includes a wide range of image examples is applied as prior knowledge to obtain the PCA bases. Here a human body scanning system is used as an example to investigate the compressive sensing performance using PCA generated radiation patterns. 11880 different gray scale images (75×100 pixels) of different people with different height, at different locations, carrying and without carrying threat weapon are applied as a statistical library. The image resolution/pixel size is 2 cm×2 cm. PCA is used to obtain the best projection bases to represent this library. Several example images in the statistical library are shown in FIG. 3. In practice, an actual implementation would use radio frequency ("RF") images to train the PCA library. The optical images used here were surrogates for the more desirable RF data. FIG. 4 shows the first few principal components obtained using PCA. It is well known that the image energy is strongly biased toward low order PCA generated components. This then is a form of sparsity, which allows very good reconstructions to be obtained from only a few measurements of the lowest order PCA projection. These PCA generated bases are applied as the measurement bases in the compressive sensing algorithm. The compressive sensing optimization algorithm applied here is TwIST [4]. FIG. 5 illustrates the original object images without (top) and with threat (bottom) compared to the compressive sensing reconstructed images using ideal PCA generated bases and randomly generated bases. Both images are reconstructed using 200 bases, where each base represents a measurement. It can be seen clearly that the reconstructed image using PCA generated bases has much better performance than that using randomly generated bases. Basically, with the small number of measurements, it is hard to obtain much information in the random base reconstructed image.

Figure 6:
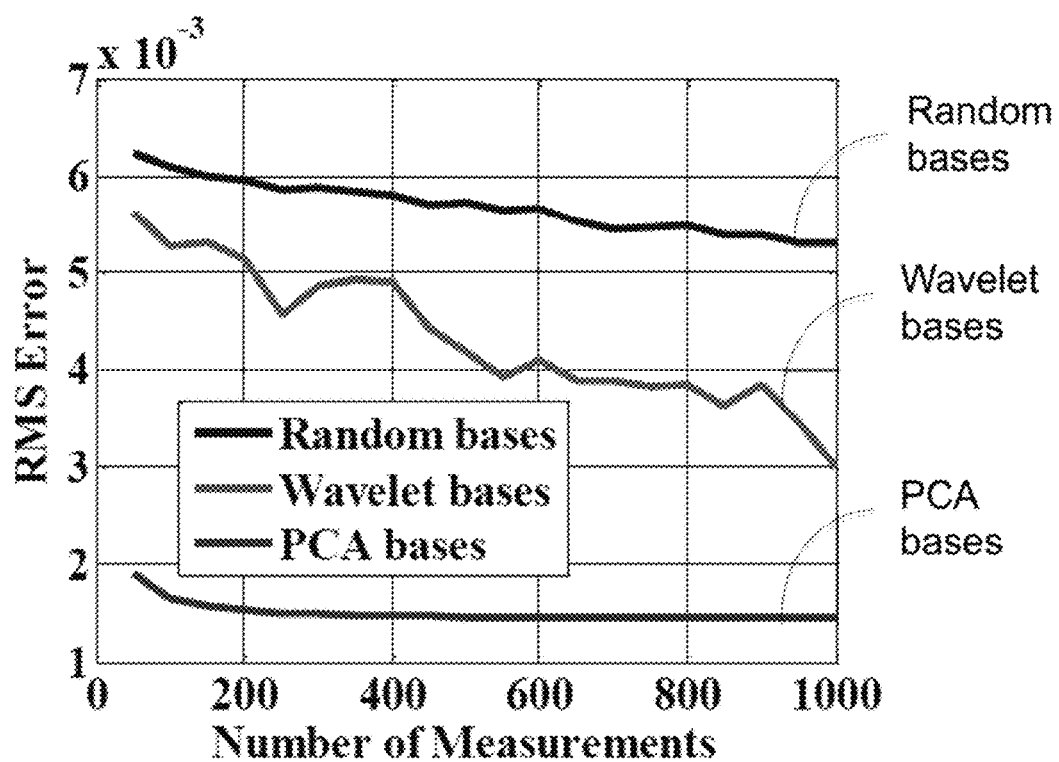
FIG. 6 shows the root mean square ("RMS") error of the compressive sensing reconstructed images using randomly generated bases, wavelet bases and PCA generated bases.

FIG. 6 plots the RMS error of the compressive sensing reconstructed image with different number of measurements from 50 to 1000 using randomly generated bases, Harr wavelet bases and PCA generated bases. The RMS error of the PCA based compressive sensing system is several times smaller than the RMS error of the random or wavelet based compressive sensing system for all cases (50 to 1000 measurements).

II. Realizing PCA Generated Radiation Patterns by Reconfigurable Array

A. Reconfigurable Array to Control the Field Distribution

To implement the optimum bases generated by PCA, a reconfigurable array aperture is designed to realize the resulting radiation patterns. By varying the phase and amplitude distribution of the reconfigurable array aperture, the radiation pattern of the aperture and the projected field on the object scene can be controlled. Each projected field distribution thus represents a measurement of the scene.

If the object image is defined as $O_i(\vec{r}_s)$, the radiated field on the scene as $U(\vec{r}_s)$, the measured reflection coefficient $m_i$ of the array will be proportional to $$\frac{j}{\beta_0} \sum_{r_s} [U(\vec{r}_s)]^2 O_i(\vec{r}_s).$$

By setting appropriate amplitude and phase to achieve $[U(\vec{r}_s)]^2$ equal to the PCA generated bases, a discrete set of measurements can be performed and compressive sensing algorithm can be used to estimate information of the scene.

Figure 7:
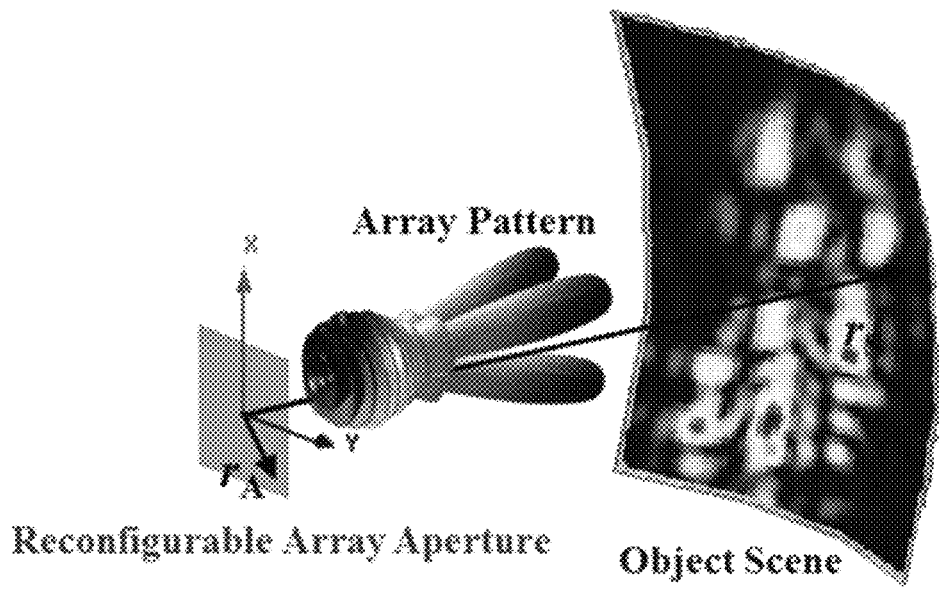
FIG. 7 is a schematic illustration of a reconfigurable array system.

A schematic picture of a reconfigurable array is shown in FIG. 7. In this example, a 40×40-element reconfigurable array with a unit cell size 4 mm×4 mm is employed to generate the desired radiation patterns. The operating frequency is at 30 GHz. The scene is selected to be a surface with equal distance to the origin (center of the array) to minimize the distance induced phase difference of the projected field on the scene. The distance from the origin to the scene is 1.6 meters ("m").

B. Beam Synthesis Algorithm to Control the Projected Field

Considering the object scene in the far-field region of a single element on the array aperture, the field distribution U($\vec{r}_s$) on the scene can be approximately calculated using:

$$U(\vec{r}_s) \propto \sum_{\vec{r}_A} A(\vec{r}_A) e^{jP(\vec{r}_A)} \cdot e^{-jkR(\vec{r}_A)} / R(\vec{r}_A), \quad (1)$$

where $A(\vec{r}_A)$ and $P(\vec{r}_A)$ are the amplitude and phase distribution of each element on the reconfigurable array. $R(\vec{r}_A)$ is the distance from the array element to the object, which can be calculated using $\vec{r}_S - \vec{r}_A$.

To synthesize the beam and control the projected field on the object, an iteration method [5] to optimize the radiated field was applied. First, the required energy field ("E-field") distributions on the object scene generated by PCA were converted into far-field distributions. After that, a far field beam synthesis method [5] was applied to find out the required amplitude and phase distribution of the array elements to achieve this far field distribution for the first iteration. Then, these calculated amplitude and phase distributions of the array elements were inserted into Eq. (1) to evaluate the achieved field distribution on the object. The first iteration result may not be able to generate the perfect required E-field distribution on the object scene because the object is not in the far field region of the whole aperture and the number of elements on the array aperture is not infinite. However, using an intersection approach in [5], a new field distribution that is between the perfect pattern and the achieved pattern can be calculated and applied back to the second iteration process. After several iterations, the optimized amplitude and phase distributions of array elements can be obtained.

During the iteration process, a mandatory requirement on the amplitude distribution, (e.g. a uniform amplitude distribution), of the array element can be applied. Therefore, the beam synthesis of a reconfigurable array with phase only control can also be realized since the implementation of a phase-only array is much easier compared to an array that needs both amplitude and phase controls. In the following section, the beam synthesis results using both amplitude and phase controls and phase only control are compared.

C. Reconfigurable Array to Realize PCA Generated Bases

Figure 8:
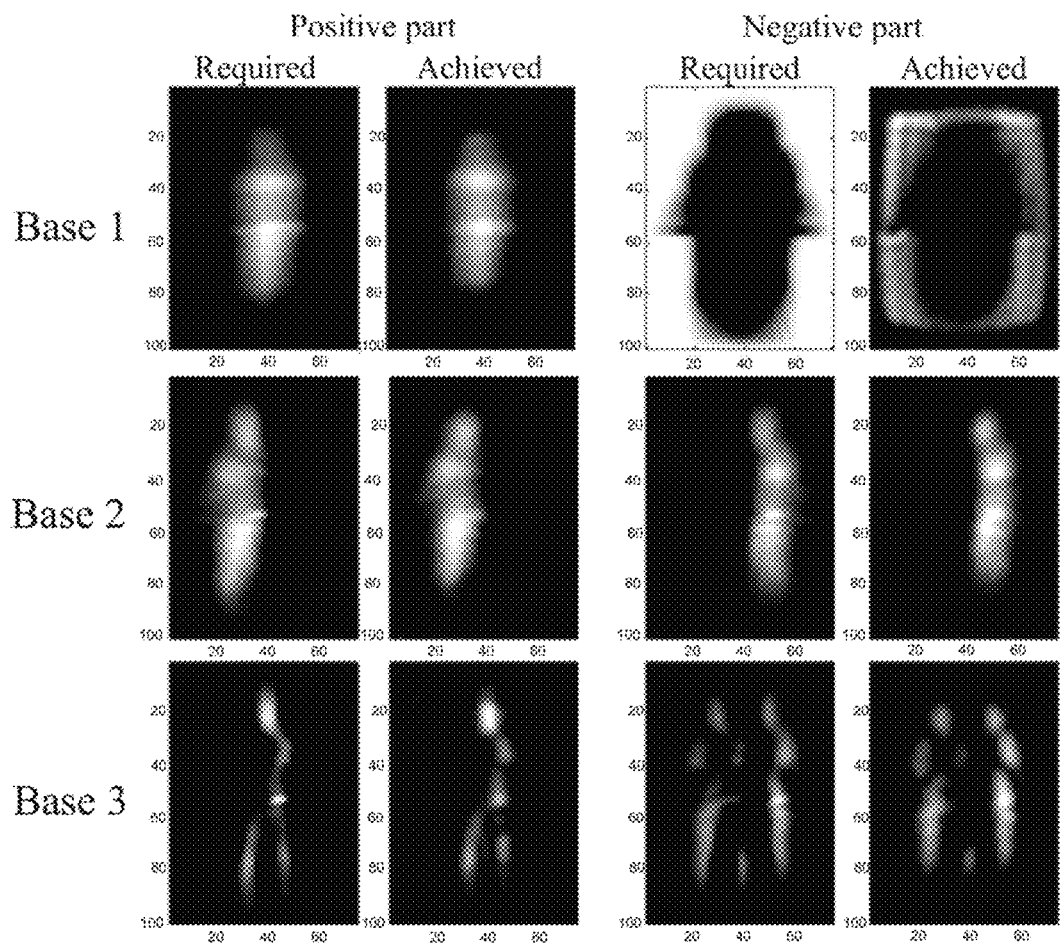
FIG. 8 shows the positive part and negative part of the beam synthesis results to realize the first three bases generated from PCA using both amplitude and phase controls.
Figure 9:
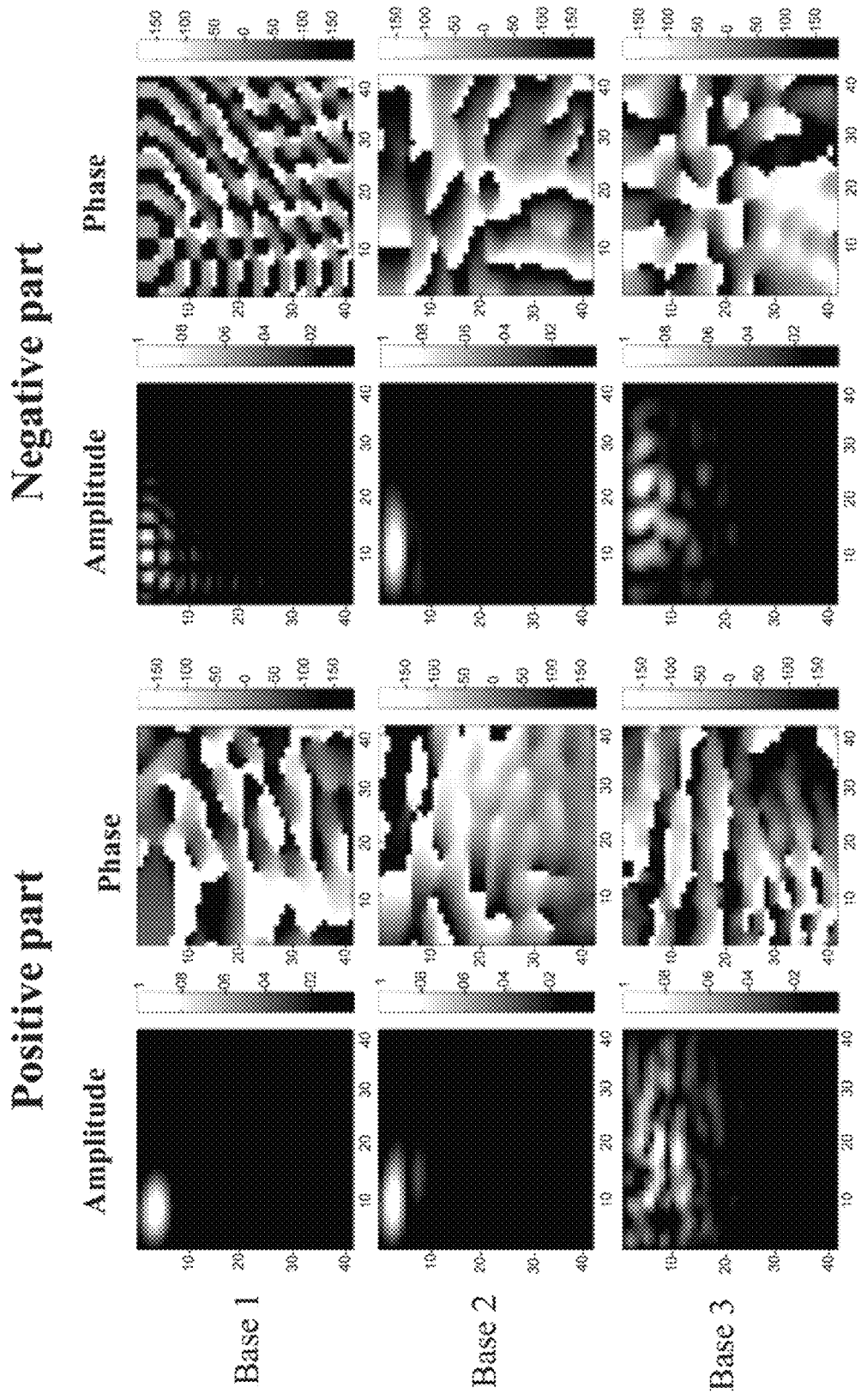
FIG. 9 shows the amplitude and phase distribution of the array elements to achieve the patterns in FIG. 8.

From the PCA generated principle components using the previously mentioned statistical image library, there are both positive and negative values in the generated bases (i.e., 180 degree phase difference in the E-field distribution). Since it is not easy to implement both positive and negative values using a single pattern, a dual-rail approach [6] is employed in which all the PCA generated bases are separated into positive and negative parts. Each part is treated as an independence base to be realized using the beam synthesis method. The results using the beam synthesis method to realize the first three bases in FIG. 4 with both amplitude and phase controls are shown in FIG. 8, while FIG. 9 plots the required amplitude and phase distribution of the array elements to achieve these patterns.

Figure 10:
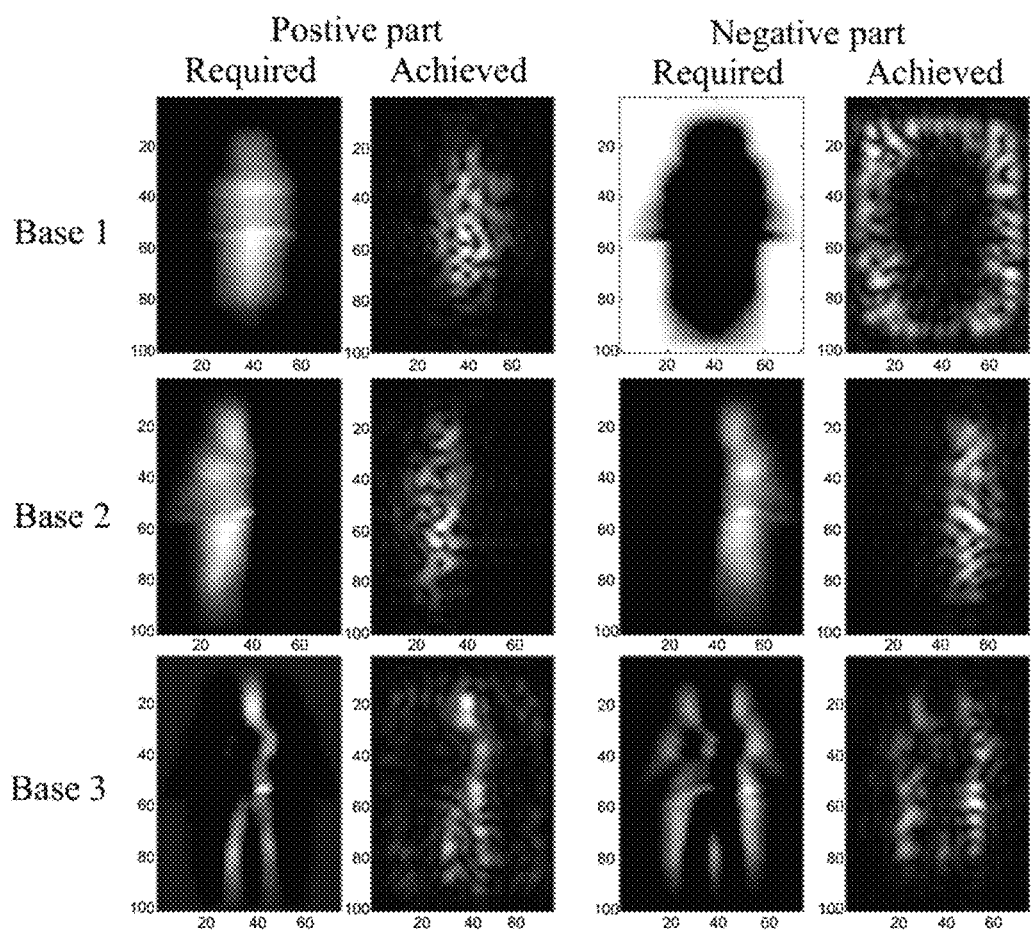
FIG. 10 shows the beam synthesis results to realize the first three bases generated from PCA using phase only control.
Figure 11:
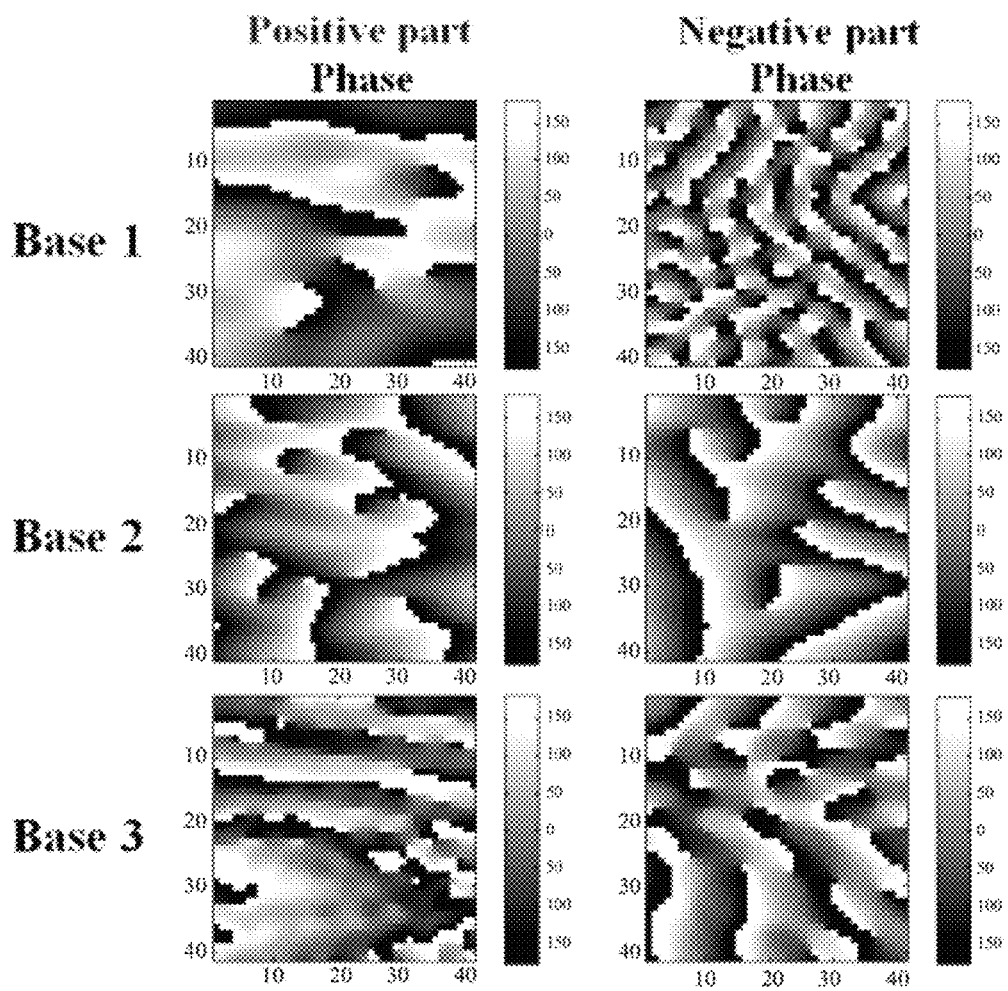
FIG. 11 shows the phase distribution of array elements used to achieve the pattern in FIG. 10.
Figure 16:
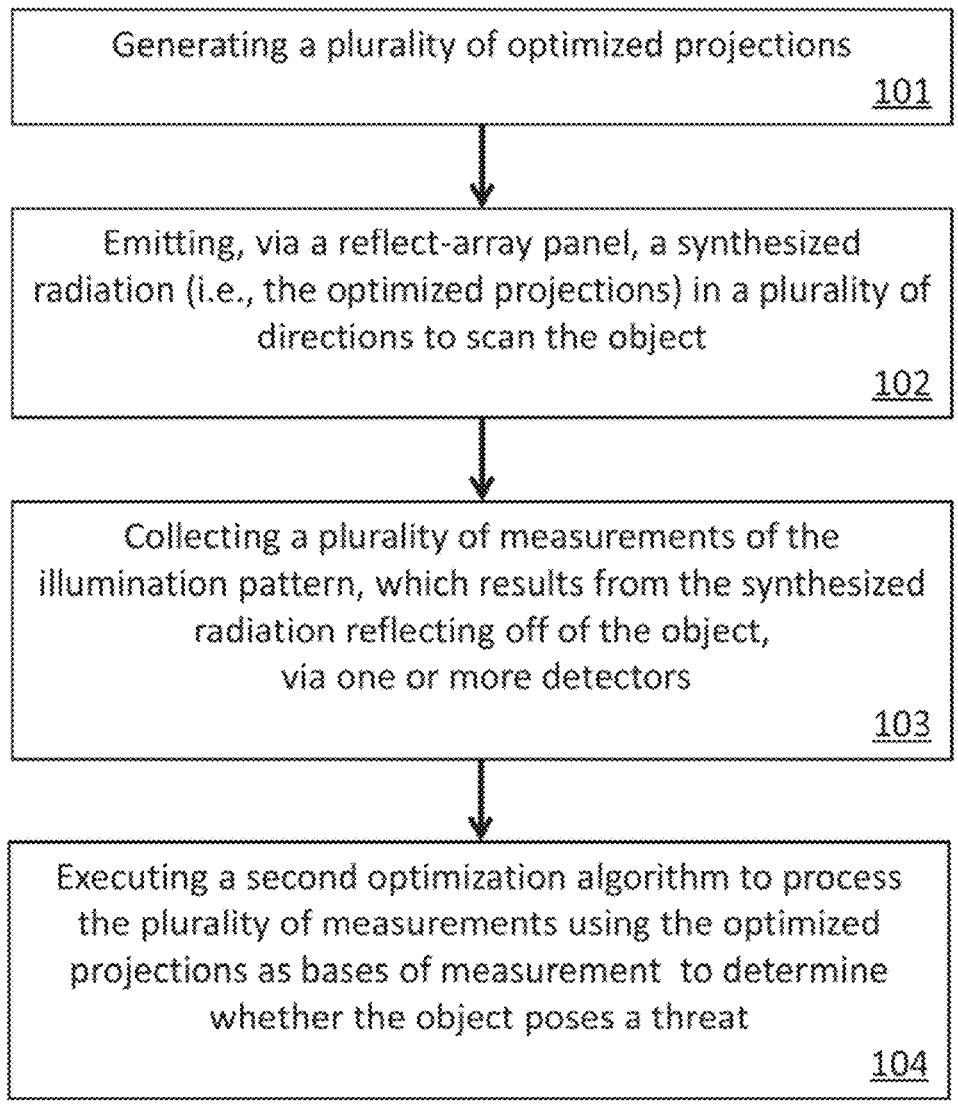
FIG. 16 shows a flowchart detailing an exemplary method for the present invention.

FIG. 10 illustrates the beam synthesis results with phase only control and FIG. 11 is the required phase distribution of the array elements. It can be seen that the achieved pattern is worse than the results using both amplitude and phase controls. However, with a uniform amplitude distribution, the reconfigurable array will be simpler and lower cost.

D. Compressive Sensing Results Using Reconfigurable Array Generated PCA Patterns After the achieved radiation patterns using the reconfigurable array are obtained, these non-ideal bases are applied in the compressive sensing algorithm to evaluate how much the pattern inaccuracies would influence the reconstructed image. To keep generality, the testing objects were not selected from the statistical library. Also, noises are added in the measured data, having a 10 dB SNR. FIG. 12 shows the compressive sensing reconstructed image using 200 reconfigurable array synthesized patterns with both amplitude and phase controls (representing only 100 PCA bases because of the dual-rail approach), and the obtained image using 200 random bases. FIG. 13 plots the RMS error of the compressive sensing reconstructed images with different number of measurements using reconfigurable array generated bases, random bases and the RMS error using full data imaging method. In order to make fair comparison, the time-per-sample for the full data imaging method was reduced to keep the same total measurement time for all techniques. Therefore, the full data measurement operates at a lower corresponding SNR than compressive sensing method. Compared to images obtained using ideal PCA bases as shown in FIG. 6, the system using reconfigurable array generated PCA bases needs a greater number of measurements to achieve the same RMS error level. However, the reconfigurable array system still yields much better performance than that of random bases.

FIG. 14 and FIG. 15 plot the compressive sensing reconstructed image and its RMS errors using reconfigurable array with phase only control. It can be observed that the system performance degrades compared to the reconfigurable array with both amplitude and phase controls. Nevertheless, it still has much better performance than the compressive sensing system using random patterns.

III. Conclusions

In the present example, a PCA based microwave compressive sensing imaging system was described. Employing the reconfigurable array technique of the present invention generated the required radiation patterns from PCA. An iterative beam synthesis method was used to obtain the amplitude and phase distribution of the array elements. The compressive sensing results using both amplitude and phase controlled array and phase only controlled array were reported. Compared to compressive sensing system using random bases, this kind of PCA based system requires much smaller number of measurements to achieve the same imaging performance.

Figure 17:
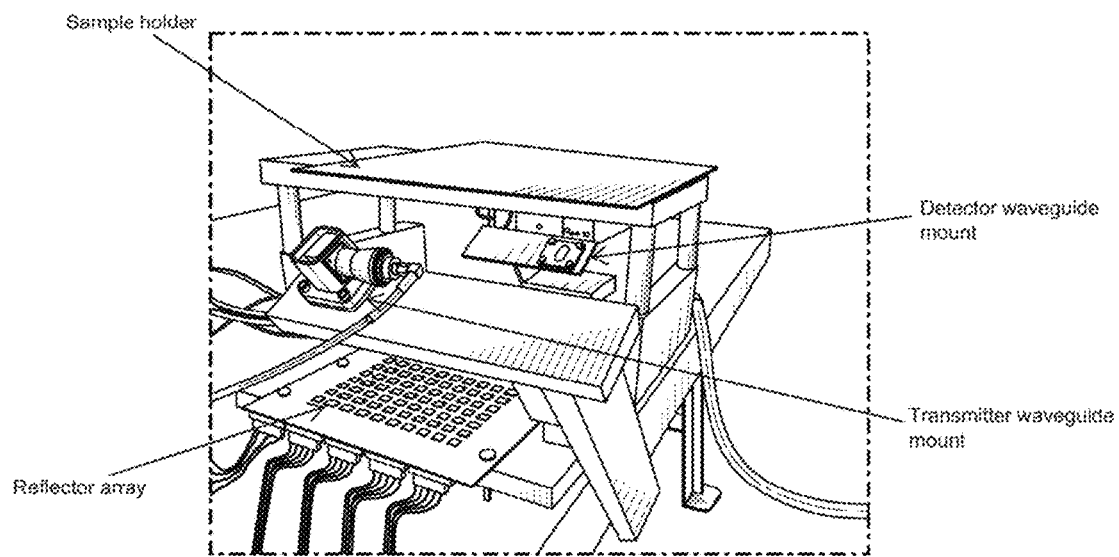
FIG. 17 shows the system configuration for the near-field measurement.

Example of the Reflect-Array Based Threat Detection System Using Millimeter-Wave Compressive Sensing During the present experiment, (1) system calibration and library construction of different materials was performed and (2) system calibration including real shoe and build library for shoe detection was performed. Performance of the reflect-array based threat detection system was verified by near-field measurements. It was confirmed that the direct current ("DC") voltage applied to the varactors controls the phase of each reflect-array element on the reflector-array panel. It was also found that these DC voltages control the radiation pattern of the reflect-array aperture. System configuration for the near field measurement was realized by integrating the reflect-array aperture, sample holder and detector mount. FIG. 17 shows the system configuration for the near field measurement. System calibration and library construction including real shoe sample was established. Threat detection experiments with different shoes were realized based on the established library information.

Figure 18:
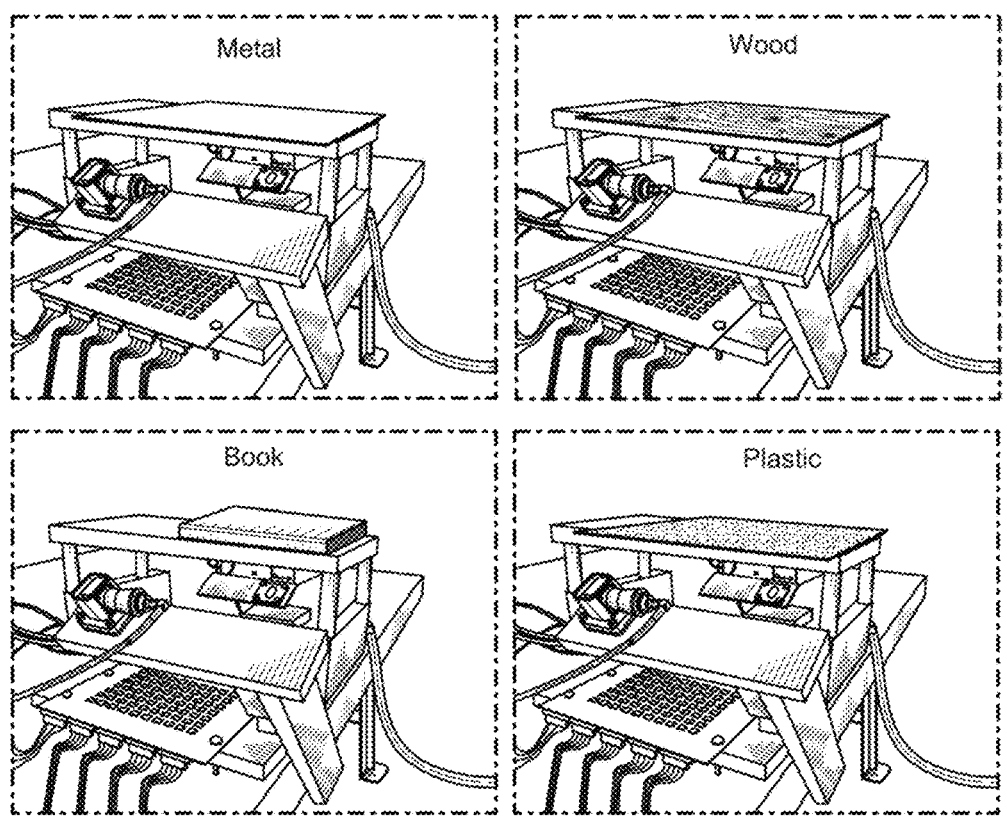
FIG. 18 shows the system configuration and examples of the near-field measurement to build the library.
Figure 19:
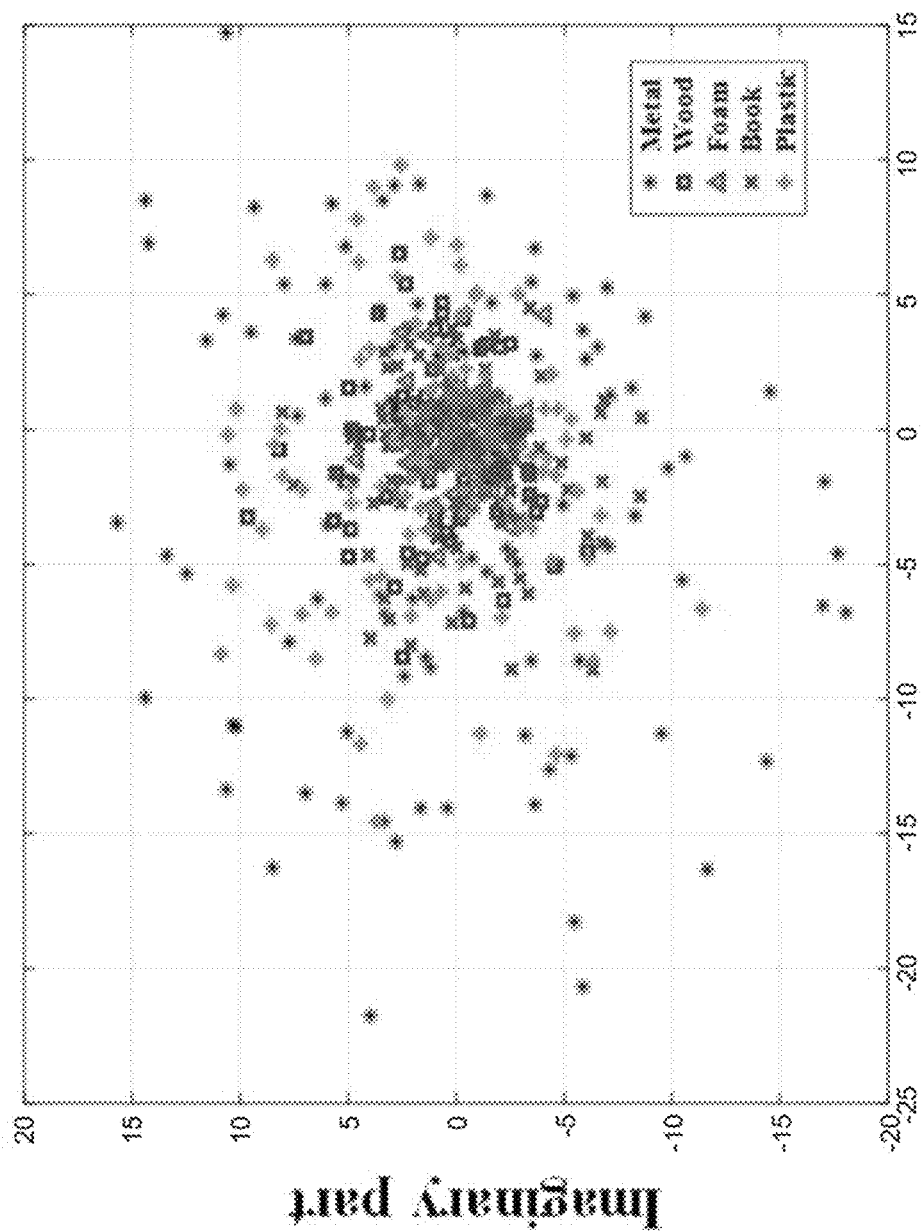
FIG. 19 shows an example of measured E-field contribution of 100 elements for different materials.

A control circuit board was fabricated to control the voltage of 100 unit cells on the reflector-array aperture. A Labview program was generated to automatically control the voltages. Detector mount and a sample holder was built and integrated together with the reflector array to perform near field measurement. Library construction for different materials such as metal, wood, paper and plastic was performed. FIG. 18 shows the experiment configuration of the near-field measurement to build the library. FIG. 19 shows the measured E-field contribution of 100 elements for different materials.

Figure 20:
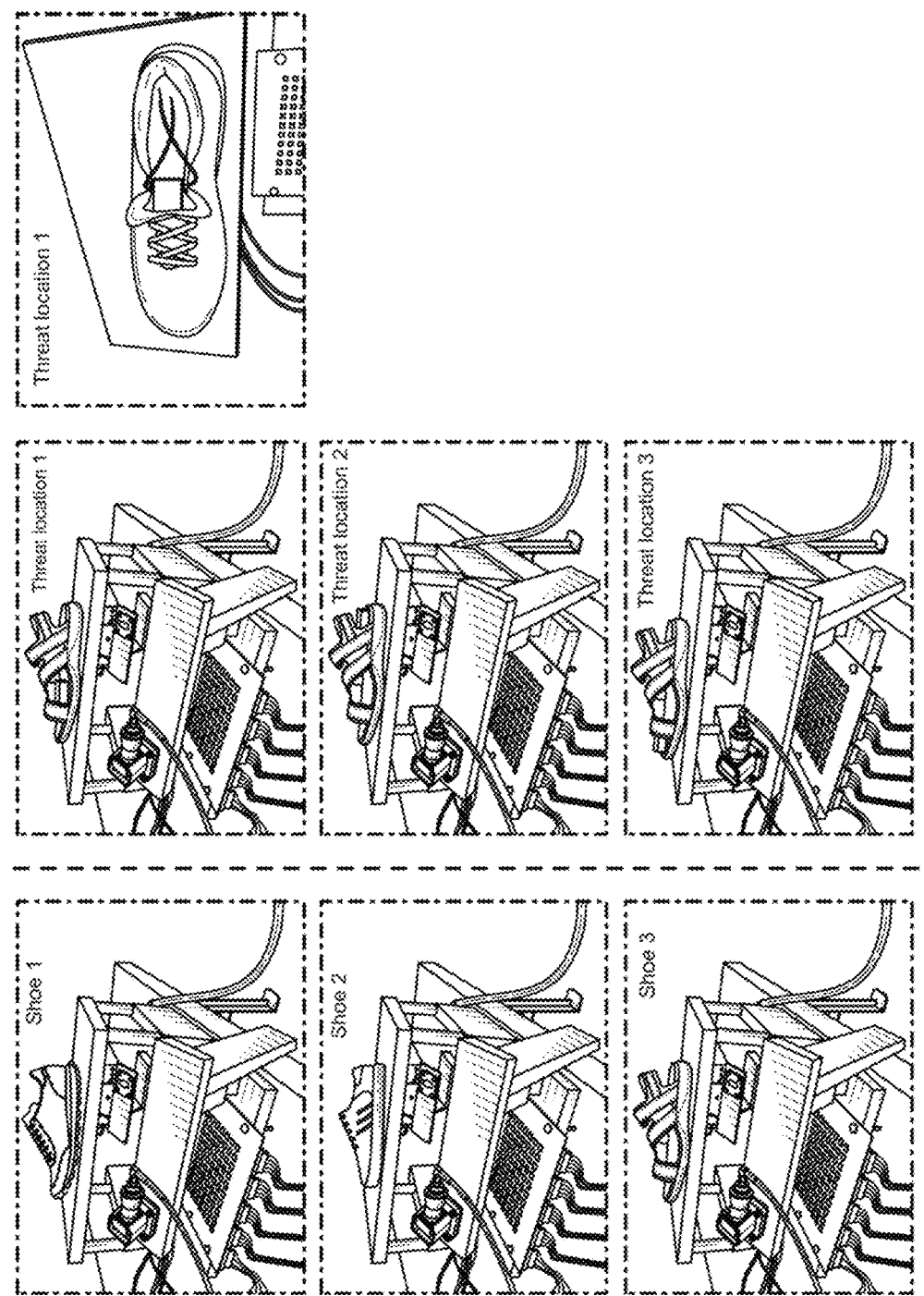
FIG. 20 shows the system configuration to test different shoe samples with and without threat object.
Figure 21:
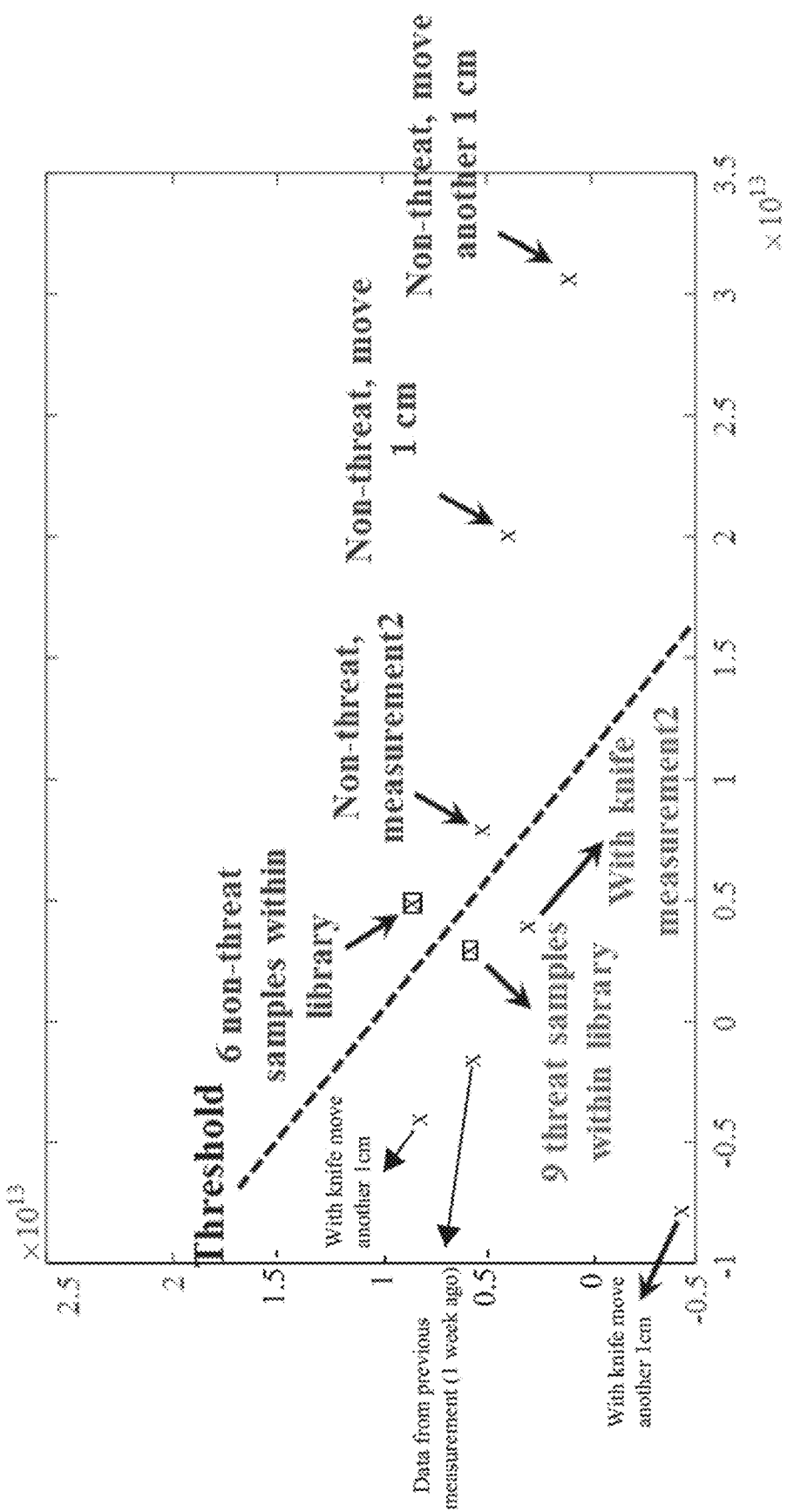
FIG. 21 shows the detection results to distinguish whether there is a threat object in the shoe sample.

Different shoe samples with and without a knife as threat were measured with the near-field system. The measured results were recorded and used to build the library for the detection experiment. Based on the library of shoe samples with and without threat object, threat detection experiment was performed. FIG. 20 shows the experiment configuration to test different shoe samples with and without threat object. FIG. 21 shows the detection results to distinguish whether there is threat object in the shoe sample. From the detection results it can be clearly seen that threat objects are clearly detected from the non-threat objects.

In this example, 100 measures are needed to detect a sample. The area of the sample is about 40 cm×28 cm. If conventional methods are used to detect this area at 10 GHz (use half wavelength 1.5 cm as pixel size), 27*19=513 pixels are required. So about 5.13 times improvement for this prototype was obtained.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

1. Eldar, Yonina C; Kutyniok, Gitta, "Compressed sensing: theory and applications" Cambridge University Press, 2012.

2. J. Hunt et al, "Metamaterial Apertures for Computational Imaging" Science, Vol. 339, pp. 310-313, 2013.

3. I. T. Jolliffe, "Principal Component Analysis" New York: Springer. 2002.

4. J. M. Bioucas-Dias, and M. A. Figueiredo, "A New Twist: Two-Step Iterative Shrinkage/Thresholding Algorithms for Image Restoration," IEEE Trans. Image Process. 16, pp. 2992-3004,2007.

5. O. M. Bucci, G. Mazzarella and G. Panariello, "Reconfigurable Arrays by Phase-Only Control," IEEE Trans. on Antennas and Propagation, Vol. 39, No. 7, pp. 919-925, 1991.

6. M. A. Neifeld and P. Shankar, "Feature-specific imaging," Appl. Opt., Vol. 42, 3379-3389 (2003).

7. Payam Nayeri, Min Liang, Rafael Austreberto Sabory-Garc'ia, Mingguang Tuo, Fan Yang, Michael Gehm, Hao Xin and Atef Z. Elsherbeni "3D Printed Dielectric Reflectarrays: Low-Cost High-Gain Antennas at Sub-Millimeter Waves" IEEE Trans. on Antennas and Propagation, vol. 62, no. 4, April 2014.

8. Xin, Hao, et. al, "Reconfigurable Array Design to Realize Principal Component Analysis (PCA) Based Microwave Compressive Sensing Imaging System", IEEE Antennas and Wireless Propagation Letters, January 2015.

What is claimed is:

1. A reflect-array based threat detection system employing compressive sensing to effectively determine whether or not an object is a threat, the system comprising:
  (a) a first processor executing a first optimization algorithm using a plurality of samples to generate a plurality of optimized projections;
  (b) a library operatively coupled to the first processor, wherein the plurality of optimized projections and the plurality of samples are stored in the library, wherein the library is capable of adaptively increasing an amount of samples by adding a plurality of new measurement results to improve accuracy of threat determination accuracy;
  (c) a reflect-array panel emitting a synthesized radiation in a plurality of directions to scan the object, wherein the reflect-array panel comprises a first set of reflect-array elements, wherein each reflect-array element emits the plurality of optimized projections as a radiation pattern in one of the plurality of directions, wherein the synthesized radiation is a collective radiation comprising each radiation pattern emitted by each reflect-array element, wherein an illumination pattern results from the synthesized radiation reflecting off of the object;
  (d) one or more detectors configured to collect a plurality of measurements of the illumination pattern; and
  (e) a compressive sensing computer, operatively coupled to the one or more detectors, having a second processor configured to execute a compressive sensing optimization algorithm, herein referred to as a second optimization algorithm, wherein the second optimization algorithm processes the plurality of measurements and determines whether the object poses a threat using the plurality of optimized projections as bases of measurement.

2. The system of claim 1, wherein the plurality of samples comprises objects that pose a threat and objects that do not pose a threat.

3. The system of claim 1, wherein Principle Component Analysis, Fisher Linear Discriminant Method, Support Vectors Method, Information Optimal Method, or the K-nearest Neighbor Method is employed individually, or in combination, as the first optimization algorithm.

4. The system of claim 1, wherein Principle Component Analysis, Fisher Linear Discriminant Method, Support Vectors Method, Information Optimal Method, or the K-nearest Neighbor Method is employed individually, or in combination, as the second optimization algorithm.

5. The system of claim 1, wherein the first set of reflect-array elements comprises devices of any geometric shape having a dielectric and a conductor.

6. The system claim 1, wherein each reflect-array element, of the first set of reflect-array elements, has a phase controlled by one or more reconfigurable devices.

7. The system of claim 6, wherein a diode, a microelectromechanical systems device, or any phase changing device comprises each of the one or more reconfigurable devices.

8. The system of claim 6, wherein the synthesized radiation is determined by the phase of each reflect-array element, wherein the phase is reconfigurable.

9. The system of claim 1 further comprising a lane having a second reflect-array panel emitting a lane synthesized radiation in a set of directions to scan a second object.

10. The system of claim 9, wherein the second reflect-array panel comprises a second set of reflect-array elements each emitting the plurality of optimized projections as a radiation pattern in a direction, of the set of directions, wherein the lane synthesized radiation is a collective radiation comprising each radiation pattern emitted by each reflect-array element in the second set of reflect-array elements.

11. The system of claim 10, wherein the second set of reflect-array elements comprises devices of any geometric shape having a dielectric and a conductor.

12. The system of claim 9, wherein a second illumination pattern is produced when the lane synthesized radiation is reflected off of the second object.

13. The system of claim 9, wherein the second object is the bottom of human feet.

14. The system of claim 12, wherein a plurality of measurements of the second illumination pattern is acquired by the one or more detectors and transmitted to the compressive sensing processing computer.

15. The system of claim 14, wherein the second processor is further configured to execute a third optimization algorithm, wherein the third optimization algorithm processes the plurality of measurements of the second illumination pattern and determines whether the second object poses a threat using the optimized projections as bases of measurement.

16. The system of claim 9, wherein Principle Component Analysis, Fisher Linear Discriminant Method, Support Vectors Method, Information Optimal Method, or the K-nearest Neighbor Method is employed individually, or in combination, as the third optimization algorithm.

17. The system of claim 9 further comprising a plurality of lanes.

18. The system of claim 1, wherein the reflect-array panel scans a plurality of objects at one time.

19. The system of claim 1 further comprising a two-sided reflect-array panel configured to scan an object on each side of the two-sided reflect-array panel.

20. A method for reflect-array based threat detection employing compressive sensing to effectively determine whether an object is a threat, the method comprising:

(a) generating a plurality of optimized projections, wherein the plurality optimized projections result from executing a first optimization algorithm, via a first processor, using a plurality of samples as bases of measurement, wherein a library, operatively coupled to the first processor, stores the plurality of optimized projections;

(b) emitting a synthesized radiation in a plurality of directions to scan the object via a reflect-array panel, wherein the reflect-array panel comprises a set of reflect-array elements, wherein each reflect-array element emits the plurality of optimized projections as a radiation pattern in one of the plurality of directions, wherein the synthesized radiation is a collective radiation comprising each radiation pattern emitted by each reflect-array element, wherein an illumination pattern results from the synthesized radiation reflecting off of the object;

(c) collecting a plurality of measurements of the illumination pattern via one or more detectors; and (d) executing a second optimization algorithm, alternately referred to herein as a compressive sensing optimization algorithm, via a second processor operatively coupled to the one or more detectors, wherein the compressive sensing optimization algorithm processes the plurality of measurements and determines whether the object poses a threat using the plurality of optimized projections as bases of measurement.

* * * * *